(12) United States Patent
Rossetto et al.

(10) Patent No.: US 8,343,149 B2
(45) Date of Patent: Jan. 1, 2013

(54) DEPLOYABLE MICROWAVE ANTENNA FOR TREATING TISSUE

(75) Inventors: Francesca Rossetto, Longmont, CO (US); Mani N. Prakash, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 1207 days.

(21) Appl. No.: 12/147,093

(22) Filed: Jun. 26, 2008

(65) Prior Publication Data

US 2009/0326620 A1    Dec. 31, 2009

(51) Int. Cl.
*A61B 18/18* (2006.01)
*A61B 18/04* (2006.01)
*A61F 2/00* (2006.01)

(52) U.S. Cl. ............ 606/50; 606/33; 607/101; 607/156

(58) Field of Classification Search .............. 606/27–50; 607/96–102, 105, 113; 343/790, 791
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| 4,815,479 A | 3/1989 | Carr | |
| 5,281,217 A | 1/1994 | Edwards et al. | |
| 5,800,494 A | 9/1998 | Campbell et al. | |
| 5,871,525 A | 2/1999 | Edwards et al. | |
| 6,014,581 A | 1/2000 | Whayne et al. | |
| D424,694 S | 5/2000 | Tetzlaff et al. | |
| D425,201 S | 5/2000 | Tetzlaff et al. | |
| 6,221,039 B1 | 4/2001 | Durgin et al. | |
| 6,245,062 B1 | 6/2001 | Berube et al. | |
| D449,886 S | 10/2001 | Tetzlaff et al. | |
| 6,358,245 B1 | 3/2002 | Edwards et al. | |
| D457,958 S | 5/2002 | Dycus et al. | |
| D457,959 S | 5/2002 | Tetzlaff et al. | |
| 6,506,189 B1 | 1/2003 | Rittman, III et al. | |
| 6,722,371 B1 | 4/2004 | Fogarty et al. | |
| D496,997 S | 10/2004 | Dycus et al. | |
| D499,181 S | 11/2004 | Dycus et al. | |
| 6,962,586 B2 * | 11/2005 | Berube et al. | 606/33 |

(Continued)

FOREIGN PATENT DOCUMENTS

DE    390937    3/1924

(Continued)

OTHER PUBLICATIONS

U.S. Appl. No. 08/483,742, filed Jun. 7, 1995.

(Continued)

*Primary Examiner* — Nicholas Lucchesi
*Assistant Examiner* — Leah Stohr

(57) ABSTRACT

A microwave ablation system for treating tissue includes an assembly of antennas adapted to connect to a microwave generator. The microwave generator generates microwave energy. Each antenna of the assembly of antennas includes inner and outer conductors. The inner conductor has a length. The outer conductor has a longitudinal axis defined along a length thereof. The outer conductor at least partially surrounding the inner conductor at least partially along the length thereof. One of the inner conductor and the outer conductor is movable with respect to the other. At least one antenna of the assembly of antennas is deployable from a first state for ablating a first ablation region of tissue to a second deployable state for ablating a second ablation region of tissue. The first and second ablation tissue regions overlap to define an aggregate ablation region.

16 Claims, 10 Drawing Sheets

U.S. PATENT DOCUMENTS

| | | |
|---|---|---|
| D525,361 S | 7/2006 | Hushka |
| D531,311 S | 10/2006 | Guerra et al. |
| 7,128,739 B2 | 10/2006 | Prakash et al. |
| D533,942 S | 12/2006 | Kerr et al. |
| D535,027 S | 1/2007 | James et al. |
| 7,195,629 B2 | 3/2007 | Behl et al. |
| 7,197,363 B2 | 3/2007 | Prakash et al. |
| D541,418 S | 4/2007 | Schechter et al. |
| D541,938 S | 5/2007 | Kerr et al |
| 7,229,438 B2 | 6/2007 | Young |
| 7,306,595 B2 | 12/2007 | Ostrovsky et al. |
| 7,311,703 B2 | 12/2007 | Turovskiy et al. |
| D564,662 S | 3/2008 | Moses et al. |
| 7,387,628 B1 | 6/2008 | Behl et al. |
| 2003/0109868 A1 | 6/2003 | Chin et al. |
| 2005/0149010 A1 | 7/2005 | Turovskiy et al. |
| 2005/0245920 A1 | 11/2005 | Vitullo et al. |
| 2006/0217702 A1 | 9/2006 | Young |
| 2007/0073285 A1 | 3/2007 | Peterson |
| 2007/0198006 A1 | 8/2007 | Prakash et al. |
| 2007/0203486 A1 | 8/2007 | Young |
| 2007/0282325 A1 | 12/2007 | Young et al. |
| 2007/0288079 A1 | 12/2007 | Van der Weide et al. |
| 2008/0027424 A1 | 1/2008 | DeCarlo et al. |
| 2008/0255553 A1* | 10/2008 | Young et al. ............ 606/33 |
| 2008/0319434 A1 | 12/2008 | Rick et al. |
| 2009/0131926 A1* | 5/2009 | Rusin et al. ............ 606/33 |
| 2010/0030206 A1 | 2/2010 | Brannan et al. |
| 2010/0036369 A1* | 2/2010 | Hancock ............ 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 93/20768 | 10/1993 |
| WO | WO 03/039385 | 5/2003 |
| WO | WO 03/088858 | 10/2003 |
| WO | WO 2005/011049 | 2/2005 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.

U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radio!, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shanha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.

European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

DEPLOYABLE MICROWAVE ANTENNA FOR TREATING TISSUE

BACKGROUND

1. Technical Field

The present disclosure relates generally to a microwave antenna that can treat tissue. More particularly, the present disclosure is directed to a microwave antenna suitable for use in resection of tissue.

2. Background of Related Art

Treatment of certain diseases requires destruction of malignant tissue growths (e.g., tumors) or surrounding tissue. It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat, ablate and/or coagulate tissue. Microwave energy is sometimes utilized to perform these methods. In particular, microwave energy is used to coagulate or ablate tissue. Another method used to treat diseased tissue is to resect a portion of the diseased organ, tissue or anatomical structure. For example, a liver may contain diseased tissue and healthy tissue. One treatment option is to pre-coagulate and ablate some of the liver tissue to facilitate resection of a portion of the liver including the diseased tissue. Microwave energy can be used during these types of procedures to pre-coagulate tissue prior to resection, to reduce bleeding during resection and to facilitate the actual resection of the tissue.

The microwave energy may be applied via antennas that can penetrate tissue. There are several types of microwave antennas, such as monopole and dipole antennas. In monopole and dipole antennas, most of the microwave energy radiates perpendicularly away from the axis of the conductor. A monopole antenna includes a single, elongated conductor that transmits the microwave energy. A typical dipole antenna has two elongated conductors parallel to each other and positioned end-to-end relative to one another with an insulator placed therebetween. Each of the conductors is typically about ¼ of the length of the wavelength of the microwave energy making the aggregate length of both conductors about ½ of the wavelength of the microwave energy.

A coaxial dipole antenna typically includes a first elongated conductor and a second elongated conductor disposed concentrically around the first elongated conductor along about half of the distance of the coaxial assembly. The portion having the second elongated conductor is about ¼ of a wavelength and the portion having only the first elongated conductor is also about ¼ of a wavelength, making the aggregate length of the antenna about a ½ wavelength. By selecting the microwave energy wavelength to be twice the length of the dipole, power is more efficiently transmitted from the antenna to the surrounding tissue.

Some microwave antennas have a narrow operational bandwidth, a wavelength range at which operational efficiency is achieved, and hence, are incapable of maintaining a predetermined impedance match between the microwave delivery system (e.g., generator, cable, etc.) and the tissue surrounding the microwave antenna. More specifically, as microwave energy is applied to tissue, the dielectric constant of the tissue immediately surrounding the microwave antenna decreases as the tissue is heated. This drop may cause the optimal microwave energy wavelength to change beyond the bandwidth of the antenna. As a result, there may be a mismatch between the bandwidth of conventional microwave antennas and the microwave energy being applied.

SUMMARY

The present disclosure relates generally to a microwave antenna that can treat tissue. More particularly, the present disclosure is directed to a microwave antenna suitable for use in resection of tissue.

In an embodiment of the present disclosure, a microwave ablation system for treating tissue includes an assembly of antennas. The antennas of the assembly of antennas connect to a microwave generator that is configured to generate microwave energy. Each antenna of the assembly of antennas includes inner and outer conductors. The inner conductor has a length. The outer conductor has a longitudinal axis defined along a length thereof. The outer conductor at least partially surrounds the inner conductor at least partially along a length thereof. One of the inner and outer conductors is movable with respect to the other. A tapered end is disposed at the distal end of the inner conductor and/or the outer conductor. A dielectric material layer is at least partially disposed between the inner and outer conductor. At least one antenna of the assembly of antennas is deployable from a first state to a second deployable state. The first state ablates a first ablation region of tissue and the second deployable state ablates a second ablation region of tissue. The first and second ablation tissue regions may overlap to define an aggregate ablation region.

In another embodiment of the present disclosure, at least two of the assembly of antennas has two overlapping aggregate ablation regions to at least partially form an ablation plane. Two or more antennas of the assembly of antennas may have parallel longitudinal axes. The longitudinal axes of the assembly of antennas may be approximately parallel. The longitudinal axes of the assembly of antennas may be disposed in a planar region. Additionally or alternatively, each of the aggregate ablation regions of each of the assembly of antennas overlaps to at least partially form a curved plane. The assembly of antennas may be positioned to form, at least partially, a concentric ablation plane.

In yet another embodiment of the present disclosure, the system further includes a connection hub. The connection hub may include multiple cable connectors and each of the cable connectors is coupled to each corresponding antenna of the assembly of antennas. The connection hub may include a cable connector and a semi-rigid coaxial cable. The semi-rigid coaxial cable is coupled to an antenna of the assembly of antennas and to the cable connector.

In another embodiment of the present disclosure, the connection hub includes a cable connector; which is coupled to each antenna of the assembly of antennas. The connection hub further includes a power splitter coupled to the cable connector and to each antenna of the assembly of antennas. The power splitter is configured to direct a predetermined quantity of the microwave energy to each antenna of the assembly of antennas.

In another embodiment of the present disclosure, the system includes a microwave generator, which generates microwave energy at a plurality of wavelengths. Each antenna of the assembly of antennas has an effective wavelength that is about equal to a corresponding wavelength of the plurality of wavelengths. Additionally or alternatively, an antenna of the assembly of antennas has a variable effective wavelengths and the microwave generator varies the first wavelength to be about equal to the variable effective wavelength of the antenna of the assembly of antennas.

In another embodiment of the present disclosure, a method of treating tissue includes the step of providing an antenna. The method also includes deploying the antenna to a first state and ablating a first ablation regions. The method deploys the antenna to a second deployable state and ablates a second region. The first and second ablation regions overlap to define an aggregate ablation region. The step of deploying the antenna to the first state mid the step of ablating the first ablation region may be staggered or may occur sequentially. The microwave energy can be delivered to the tissue as the antenna is deployed from the first state to the second deployable state. Additionally or alternatively, the antenna has a variable effective wavelength and the microwave energy is varied to be about equal to the variable effective wavelength (this step may be skipped in some embodiments).

In yet another embodiment of the present disclosure, an antenna includes inner and outer conductors. The inner conductor includes a length. The outer conductor having a longitudinal axis defined along a length thereof. The outer conductor at least partially surrounding the inner conductor at least partially along the length thereof. The inner conductor or outer conductor is movable with respect to the other. The antenna is deployable from a first state for ablating a first ablation region of tissue to a second deployable state for ablating a second ablation region of tissue. The first and second ablation tissue regions overlap to define an aggregate ablation region.

BRIEF DESCRIPTION OF THE DRAWINGS

Various embodiments are described herein with reference to the drawings wherein.

DETAILED DESCRIPTION

Figure 1:
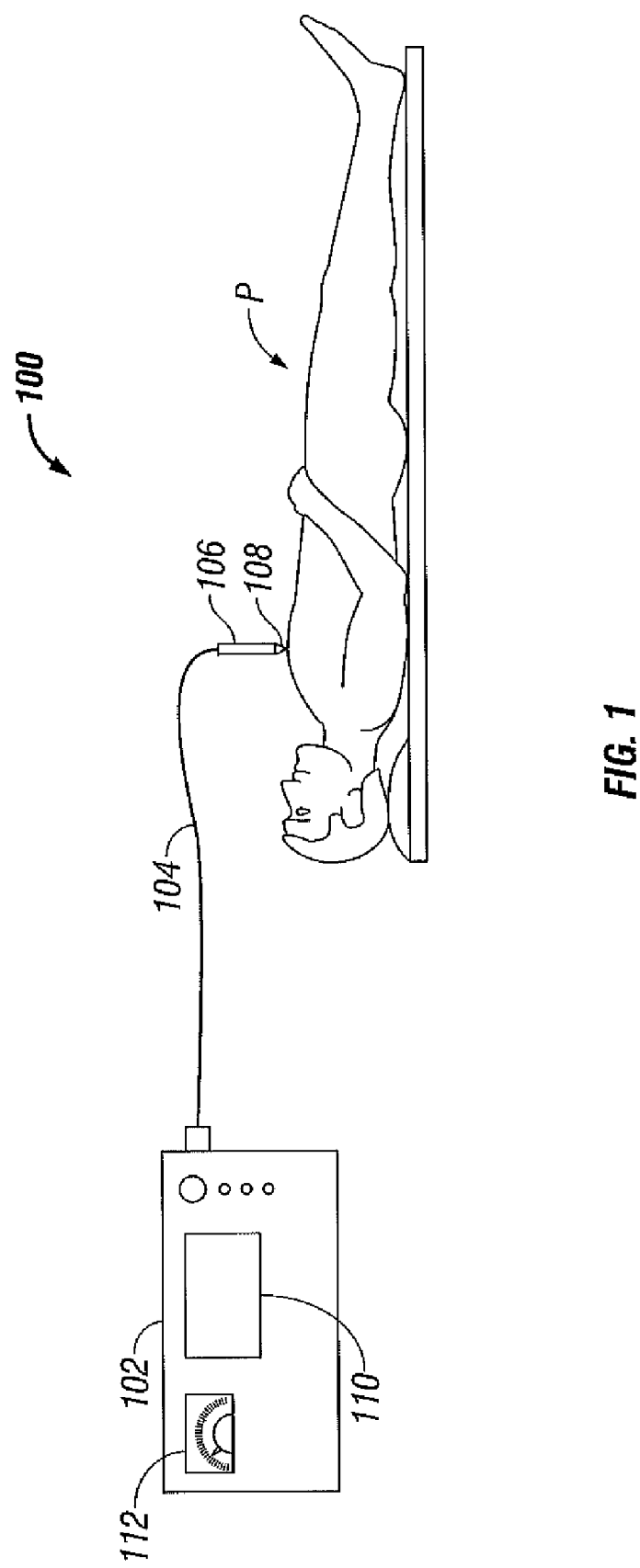
FIG. 1 is a schematic diagram of a microwave system for treating tissue in accordance with the present disclosure.

Referring to the drawings, FIG. 1 is a schematic diagram of a microwave system 100 for treating tissue using microwave energy. Microwave system 100 includes a microwave generator 102 electrically coupled to a cable 104 that can guide microwave energy to a surgical instrument 106. Surgical instrument 106 includes an antenna 108 that can treat tissue of patient P. Surgical instrument 106 may include other antennas (not depicted). Antenna 108 transmits microwave energy to tissue of patient P to ablate tissue when sufficient microwave energy is absorbed.

Microwave generator 102 includes graphical user interface 110 and dial indicator 112. Microwave generator 102 may also include other suitable input or output devices, such as knobs, dials, switches, buttons, displays and the like for control, indication and/or operation. Surgical instrument 106 may include buttons (not shown) to communicate to microwave generator 102 to generate the microwave energy. Microwave system 100 may also include a footswitch (not depicted) that connects to microwave generator 102. When actuated, the footswitch can cause microwave generator 102 to generate the microwave energy. Utilizing buttons on surgical instrument 106 or a footswitch enables the surgeon to activate the microwave energy while remaining near patient P regardless of the location of microwave generator 102.

Figure 2:
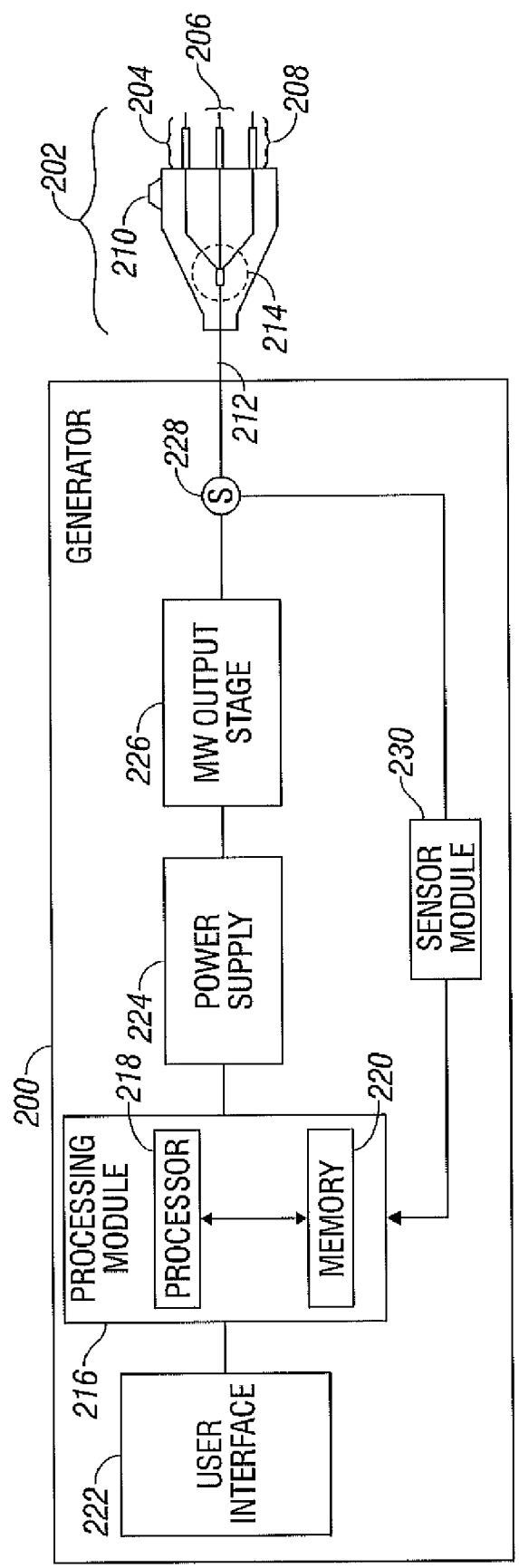
FIG. 2 is a block diagram of a microwave generator that can generate microwave energy for ablating tissue in accordance with the present disclosure.

Referring to the drawings, FIG. 2 is a block diagram of a microwave generator 200 that can generate microwave energy to treat tissue. Microwave generator 200 of FIG. 2 may be similar to or identical to microwave generator 102 of FIG. 1. Microwave generator 200 may be implemented wholly or partially in hardware, software, software in execution, bytecode, microcode, firmware, circuitry, a programmable logic device, or some sufficient combination. Microwave generator 200 may be connected to a network (e.g., the internet) and may include digital or analog connection devices, such as an RS-232 connection, an Ethernet connection or a GPIB connection.

Microwave generator 200 is connected to a surgical instrument 202 via cable 212. In the illustrated embodiment, surgical instrument 202 includes antennas 204, 206 and 208. Each of antennas 204, 206 and 208 can ablate tissue. The ablation region of each of antennas 204, 206 and 208 is a function of the deployed state (discussed in more detail below). Antennas 204, 206 and 208 may be positioned to form an ablation plane or planes for resection of tissue or organs. Surgical instrument 202 can pre-coagulate a plane of tissue along the resection line to facilitate resection of an organ or an anatomic structure. Surgical instrument 202 includes deployment control or controls 210 that can position individually (or as a group) antennas 204, 206 and 208.

Microwave generator 200 is controlled by processing module 216. Processing module 216 may also be referred to as a controller, a control module, and/or a controller board. Processing module 216 includes processor 218 and memory 220. Processor 218 may be a microprocessor, a microcontroller, logic circuitry or a semiconductor-based logic device. Memory 220 may include program data, variables, stacks, heaps and the like. Processing module 216 may include communication interfaces such as serial bus interface and a parallel bus interface, and may also include related I/O buffers, flags or associated circuitry. Additionally, processing module 216 may include analog-to-digital converters and/or digital-to-analog converters.

Processing module 216 is in operative communication with user interface 222 and can receive user data therefrom. User interface 222 may include mechanical or electrical interfaces, such as footswitches, switches, dials, screens, touch screens, speakers, microphones or the like, and associated circuitry. Processing module 216 is in operative communication with power supply 224. Power supply 224 can receive instructions from processing module 216 to supply microwave output stage 226 with sufficient power. Processing module 216 may control microwave output stage 226 directly (not depicted) or indirectly through power supply 224.

Microwave output stage 226 may output microwave energy having a single wavelength, a plurality of wavelengths or a spectrum of wavelengths. The effective wavelength of antennas 204, 206 and 208 may differ and may change based upon the deployed state, the surrounding tissue type, the surrounding tissue condition and/or the current progression of the ablation procedure. Additionally or alternatively, the effective wavelength may vary because of deployed state also varies resulting in a variable effective wavelength. Microwave output stage 226 may change a wavelength of the microwave energy to "track" or "match" an effective wavelength of one or more of antennas 204-208. Power supply 224 provides the power for microwave output stage 226 while processing module 216 controls the on/off times and/or the duty cycle. Processing module 216 may utilize one or more modulation techniques to control the microwave energy, e.g., a pulse-width modulation technique. Alternatively, processing module 216 may send a digital code to another semiconductor device (not shown), such as an ASIC chip, which generates the waveform for controlling the power supply 224.

Processing module 216 may utilize feedback to control the generation of microwave energy, such as feedback measured by sensor 228 and processed by sensor module 230. Sensor 228 may be any sensor utilized in microwave systems, such as directional couplers. Such sensors are the purview of one of ordinary skill in the art. For example, sensor 228 in conjunction with sensor module 230 can measure microwave power output, an S-parameter and/or the like. Processing module 216 may use the signal from sensor module 230 to control the generation of the microwave energy. The signal from sensor module 230 may be an analog or digital signal. For example, processing module 216 may implement a feedback-type control algorithm using the signal from sensor module 230 as an "error" signal (such as in a PID algorithm) to determine what adjustments to make to the generated microwave energy. The error signal may correspond to microwave power being delivered.

Figure 3A:
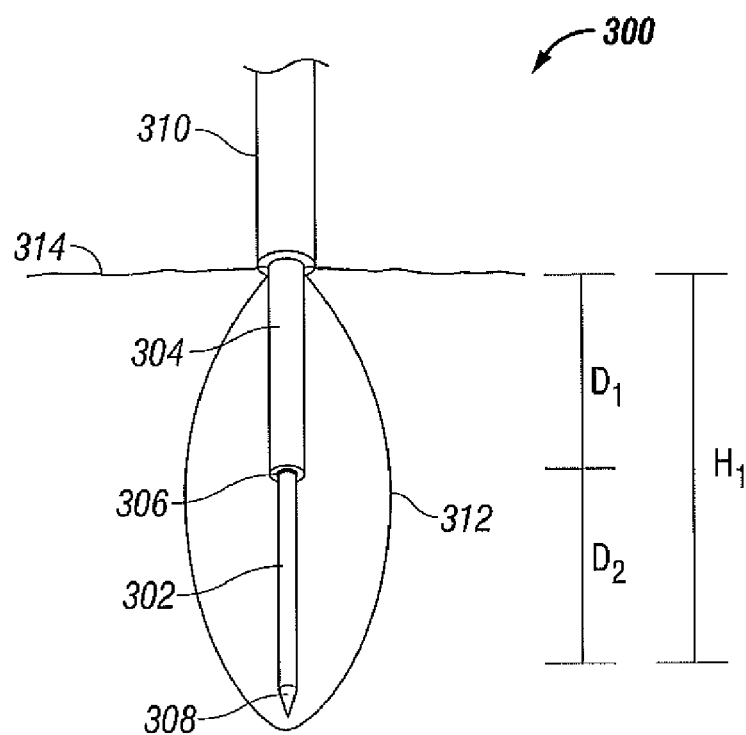
FIG. 3A is a schematic, side-view of a deployable antenna in situ that is in a balanced dipole deployment in accordance with the present disclosure.
Figure 3B:
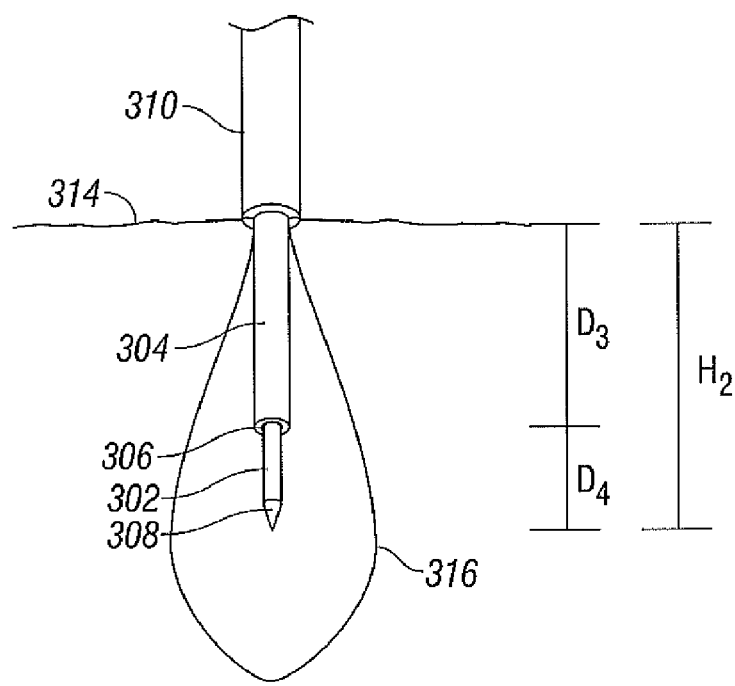
FIGS. 3B and 3C show two schematic, side-views of the deployable antenna of FIG. 3A in situ that is in an unbalanced dipole deployment in accordance with the present disclosure.
Figure 3C:
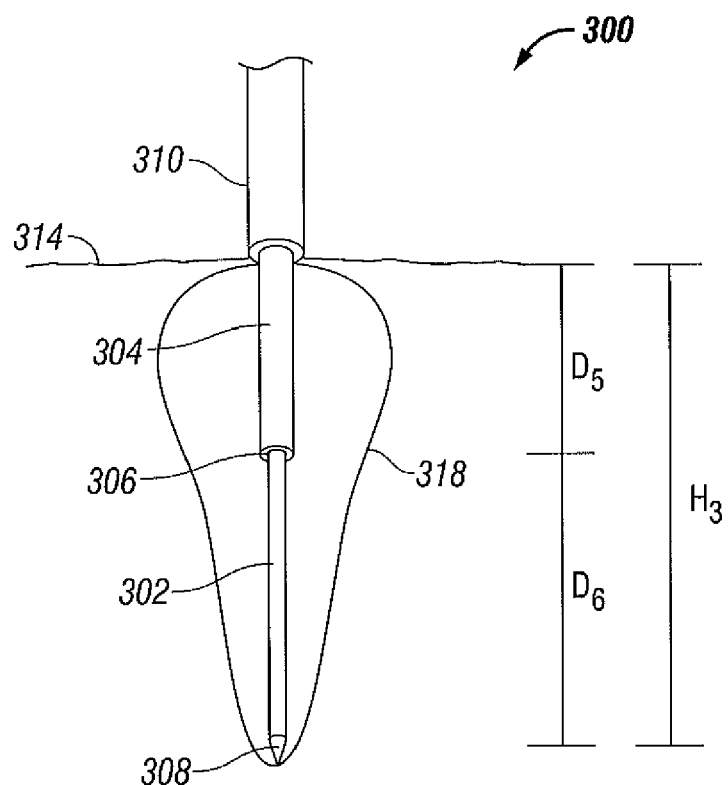

Referring to FIGS. 3A, 3B and 3C, an antenna 300 is shown in different deployed states. Antenna 300 includes a first conductor 302 and an outer conductor 304. Outer conductor 304 partially surrounds inner conductor 302, and the inner conductor 302 or the outer conductor 304 is movable relative to the other to deploy the antenna. A dielectric material layer 306 is positioned between inner conductor 302 and outer conductor 304 thus preventing direct electrical contact therebetween. Inner conductor 302 may include a tapered end 308 to facilitate piercing tissue.

Inner conductor 302 and/or outer conductor 304 may be made of a suitable conductive metal and may be semi-rigid or flexible, such as, for example, copper, gold, stainless steel or other conductive metals with similar conductivity values. Metals may be selected based on a variety of factors, such as conductivity and tensile strength. Although stainless steel has lower conductivity than copper and/or gold, stainless steel in some instruments may provide the necessary strength required to puncture tissue and/or skin. In such cases, the inner conductor 302 and/or the outer conductors 304 or portions thereof may be plated with a conductive material (e.g., copper, gold, silver, etc.) to improve conductivity and/or decrease energy loss.

As mentioned above, it is envisioned that inner conductor 302 is configured to pierce through tissue, either mechanically and/or with the aid of microwave or radio frequency energy. In the embodiment where inner conductor 302 can mechanically pierce through tissue, inner conductor 302 may be configured thin enough to pierce through tissue upon the exertion of a predetermined amount of force. Additionally or alternatively, inner conductor 302 may be configured to receive microwave energy and transmit that energy to tissue to piece through tissue or assist in piercing through tissue.

In one embodiment, inner conductor 302 is configured to move relative to outer conductor 304. In this instance, outer conductor 304 is attached to structure 310, which, in turn, is attached to a handle (not shown) that may be grasped by a surgeon for control purposes. However, in another embodiment, inner conductor 302 is attached to structure 310 such that a surgeon can move outer conductor 304 relative to inner conductor 302 and structure 310 to control the deployment state of the antenna 300. As shown in FIGS. 3A, 3B, and 3C, inner conductor 302 moves relative to outer conductor 304 and structure 310, thus changing antenna 300's deployed state.

As previously mentioned, inner conductor 302 and outer conductor 304 are separated by dielectric material layer 306 to provide insulation therebetween and may be comprised of any suitable dielectric material known in the art. Dielectric material layer 306 may be made from a ceramic material, such as alumina ceramic or a plastic material, such as a polyamide plastic (e.g., VESPEL® available from DuPont of Wilmington, Del.). Also, dielectric material layer 306 may be formed from a fluoropolymer such as tetrafluoroethylene, perfluorpropylene and the like.

As shown in FIG. 3A, tapered end 308 forms a tip at the distal end of inner conductor 302 and may be formed from a variety of heat-resistant materials suitable for penetrating tissue, such as metals (e.g., stainless steel) and various thermoplastic materials, such as poletherimide, polyamide thermoplastic resins, an example of which is Ultem® sold by General Electric Co. of Fairfield, Conn. Additionally or alternatively, tapered end 308 may be machined from various stock rods to obtain a desired shape, e.g., tapered end 308 may be a machined region of the same piece of material in which inner conductor 302 was formed. Tapered end 308 may be attached to the distal end of inner conductor 302 using various adhesives, such as an epoxy seal; if the tapered end 308 is metal, the tapered end 308 may be soldered to the distal end of inner conductor 302. As shown in FIGS. 3A, 3B and 3C, antenna 300 is inserted into tissue 314 for ablating tissue. As previously mentioned, inner conductor 302 is movable with respect to outer conductor 304 along the length of outer conductor 304.

Referring only now to FIG. 3A, antenna 300 is deployed such that outer conductor 304 is disposed in tissue 314 along a distance D1 and inner conductor 302 is disposed in tissue 314 along a distance D2. Distances D1 and D2 are approximately equal and have a combined distance of H1. Outer conductor 304 forms one radiation portion along distance D1 while inner conductor 302 forms another radiating portion along distance D2. Because D1 is approximately equal to D2, antenna 300 is in a so-called "balanced dipole deployment state", thus approximating a balanced dipole antenna. Antenna 300's deployed state affects the ablation region, which is readily seen in FIG. 3A. FIG. 3A shows antenna 300 in a balanced dipole deployment state which results in the configuration of an ablation region 312 when microwave energy is applied.

The microwave energy applied to antenna 300 is a function of the values of D1, D2 and H1. Generally, dipoles antennas are considered to have an effective wavelength that is about equal to twice the distance of H1, making the antenna a half-wavelength dipole antenna. In a half-wavelength deployment state, the applied microwave energy has a wavelength about equal to 2*H1. The effects of the deployed state, the wavelength of microwave energy applied, and the dipole antenna dimensions contribute to the antenna being considered equivalent to a double wavelength antenna, a full wavelength antenna, a half wavelength antenna, a quarter wavelength antenna, or a fraction or a multiple thereof. However, it may be desirable to utilize an effective wavelength that is not a multiple or a fraction of the total distance of H1 to shape the ablation region. Additionally or alternatively, microwave energy applied may have a wavelength chosen based upon a desired result. For example, a broadband microwave spectrum of microwave energy may be supplied to antenna 300 to allow the antenna 300's dimensions (and/or deployment) to be adjusted to match the thickness of the tissue to be resected, thus minimizing ablation time.

Referring to FIG. 3B, the deployed state is such that D4 is less than D3, resulting in a so-called "unbalanced dipole deployment". The unbalanced dipole dimensions of D3 and D4 cause the radiated microwave energy to result in an ablation region 316 when microwave energy is applied. Likewise, FIG. 3C shows a deployment state in which D6 is greater than D5 resulting in an ablation region 318. Adjusting the deployment state controls the relative ablation regions of antenna 300 (as illustrated by the different deployment states of FIGS. 3A, 3B and 3C) resulting in different ablation regions.

Figure 4A:
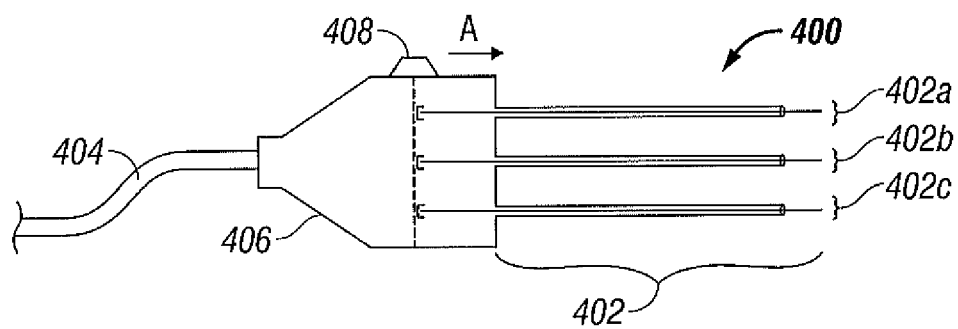
FIGS. 4A and 4B are schematic, side-views of a surgical instrument having an assembly of antennas connected to a connection hub with a single cable connector that forms an ablation plane in accordance with the present disclosure.
Figure 4B:
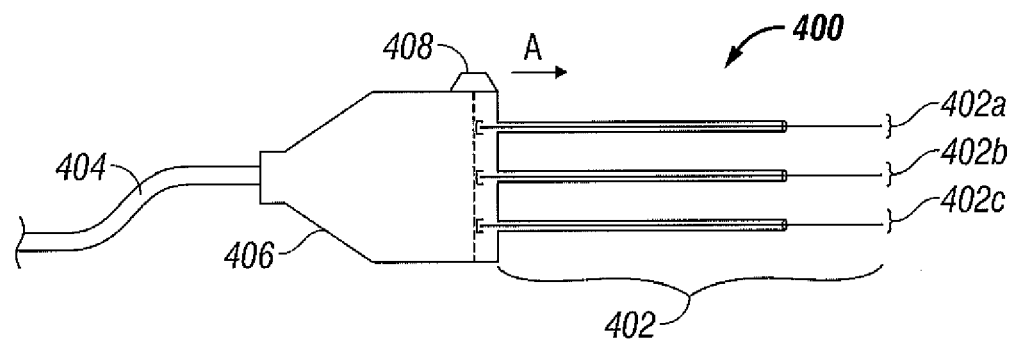

Referring to FIGS. 4A and 4B, surgical instrument 400 includes antennas 402a, 402b and 402c that form an assembly of antennas 402. Each of antennas 402a, 402b and 402c may be similar to or identical to antenna 300 of FIGS. 3A, 3B and 3C.

Surgical instrument 400 is connected to a microwave energy source by a cable 404. Housing 406 includes a connection hub (not shown) that electrically couples cable 404 to each of antennas 402a, 402b and 402e through a power splitter contained therein (not shown). However, in other embodiments, a power splitter is not used. Additionally or alternatively, a semi-rigid cable (not shown) may connect each of antennas 402a, 402b and 402c to the power splitter while ensuring ensure that the effective impedance is matched. Although housing 406 is shown as being rigid, a flexible housing may be used to facilitate various ablation or resection shapes. The deployable states of antennas 402a, 402b and 402c are simultaneously controlled by slider 408. In other embodiments, each of antennas 402a through 402c is independently controlled with a respective individual slider (not shown). FIG. 4A shows slider 408 in a first position. Slider 408 is mechanically translatable, e.g., along direction "Λ", to a second position thereby deploying antennas 402a, 402b and 402c (see FIG. 4B).

The microwave energy source may be impedance matched to the combined impedances of the cable, the internal connections, the power splitter and/or the assembly of antennas 402 (e.g., the impedances may be impedance matched to 50Ω). As the deployment state of antennas 402a, 402b and 402c are varied, the microwave energy may be intermittently applied, continuously applied, or otherwise varied. For example, while surgical instrument 400 is in a first state, microwave energy may be applied with a first frequency to maximize the power transferred to the tissue, then slider 408 may be actuated to deploy antennas 402a, 402b and 402c to a second deployable state, and a second frequency of microwave energy may be applied to again maximize the power transferred to the tissue. By repeating these steps, the ablation region of each of antennas 402a, 402b and 402c may overlap to from an aggregate ablation region. The aggregation ablation region of all of antennas 402a, 402b and 402c may overlap to form an ablation plane or planes. In this manner, surgical instrument 400 may apply microwave energy to resect tissue, organs or other anatomical structures.

Figure 5:
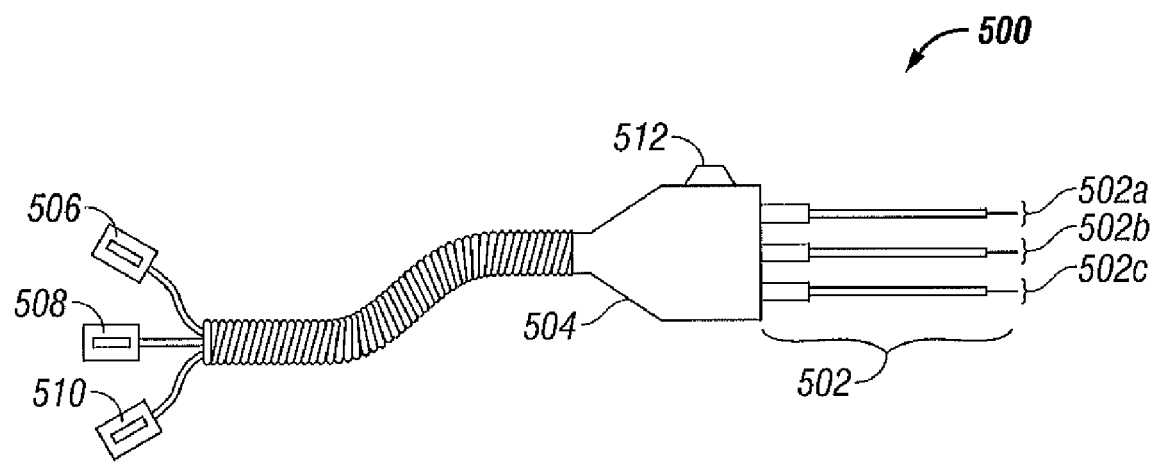
FIG. 5 shows a schematic, side-view of a surgical instrument having an assembly of antennas connected to a connection hub via a bundle of cables in accordance with the present disclosure.

FIG. 5 shows a schematic side-view of a surgical instrument 500, Surgical instrument 500 includes antennas 502a, 502b and 502c that form an assembly of antennas 502. Antenna 502 is connected to housing 504 that, in turn, connects to a hub (not shown). Although housing 504 is shown as rigid, it is contemplated that housing 504 can be flexible in other embodiments. Cables 506, 508 and 510 are electrically coupled to antennas 502a, 502b and 502c, respectively, through a connection hub (not shown) inside of housing 504. Alternatively, cables 506, 508, and 510 may be considered part of connection hub 504. Similar to surgical instrument 400, surgical instrument 500 includes a slider 512 that adjusts the deployment state of antennas 502a, 502b and 502c, simultaneously. However, in other embodiments, slider 512 is three separate sliders which each independently control one of antennas 502a through 502c. Microwave energy may be supplied individually through each of cables 506, 508 and 510. Additionally or alternatively, cables 506, 508 and 510 may be connected to a power splitter that connects to a single microwave power source (not shown).

In one embodiment, surgical instrument 500 splits the microwave energy from microwave generator 102 (see FIG. 1) with a power splitter (not shown) connected to each antennas 502a, 502b and 502c. The connecting cable (not shown) may be a common 50Ω cable and each of the semi-rigid cables 506, 508 and 510 is a N*50Ω cable (N is the number of cables); in this exemplary embodiment, each of the semi-rigid cables 506, 508 and 510 is a 150Ω cable. In another embodiment not depicted in FIG. 5, microwave generator 102 (see FIG. 1) is connected to each of antennas 502a, 502b and 502c through a separate cable; the group of cables may connect each of antennas 502a, 502b and 502c to microwave generator 102 (see FIG. 1) through a respective connection thereto.

Figure 6:
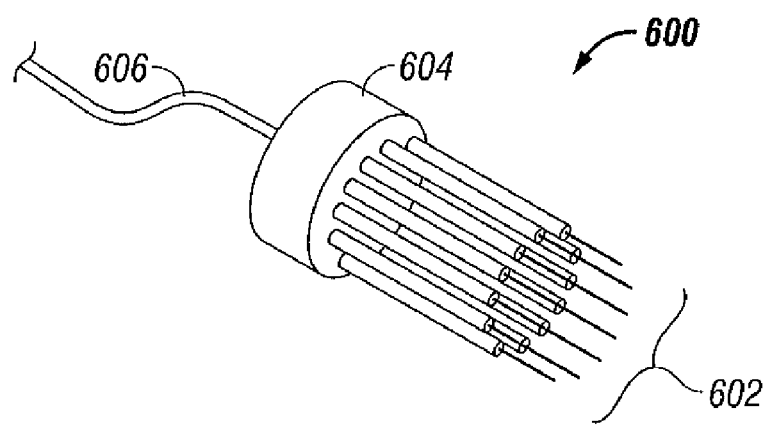
FIG. 6 shows a perspective view of a surgical instrument having an assembly of antennas each connected to a disc shaped connection hub in accordance with the present disclosure.

FIG. 6 shows a surgical instrument 600 that includes an antenna 602 connected to a housing 604. Housing 604 includes a connection hub (not shown) that electrically couples cable 606 to each of antenna of antennas 602. The impedances of surgical instrument 600 may be impedance matched to a microwave source (e.g., the impedance may be 50Ω in aggregate).

Figure 7A:
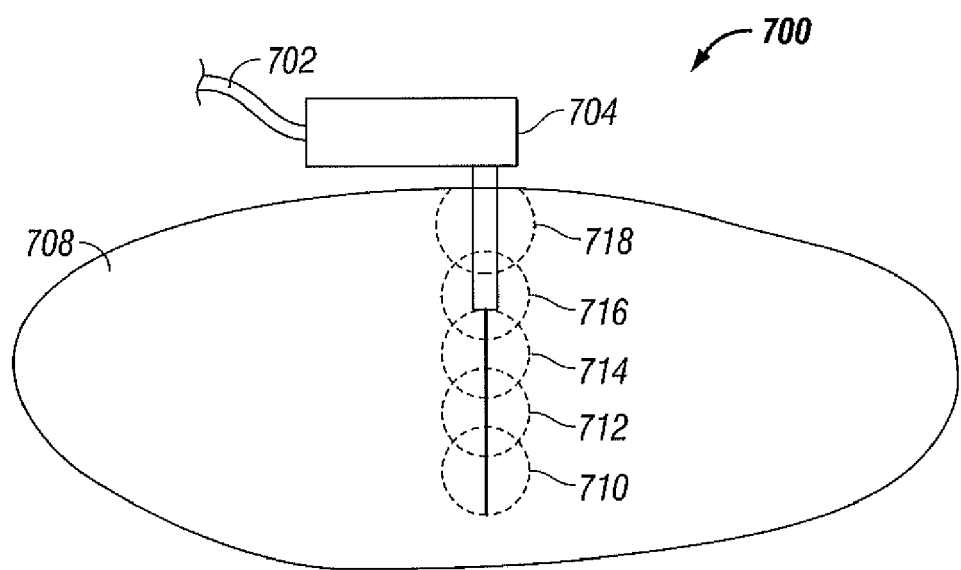
FIG. 7A shows a side view of a surgical instrument having an assembly of antennas ablating tissue to facilitate resection of tissue in accordance with the present disclosure.
Figure 7B:
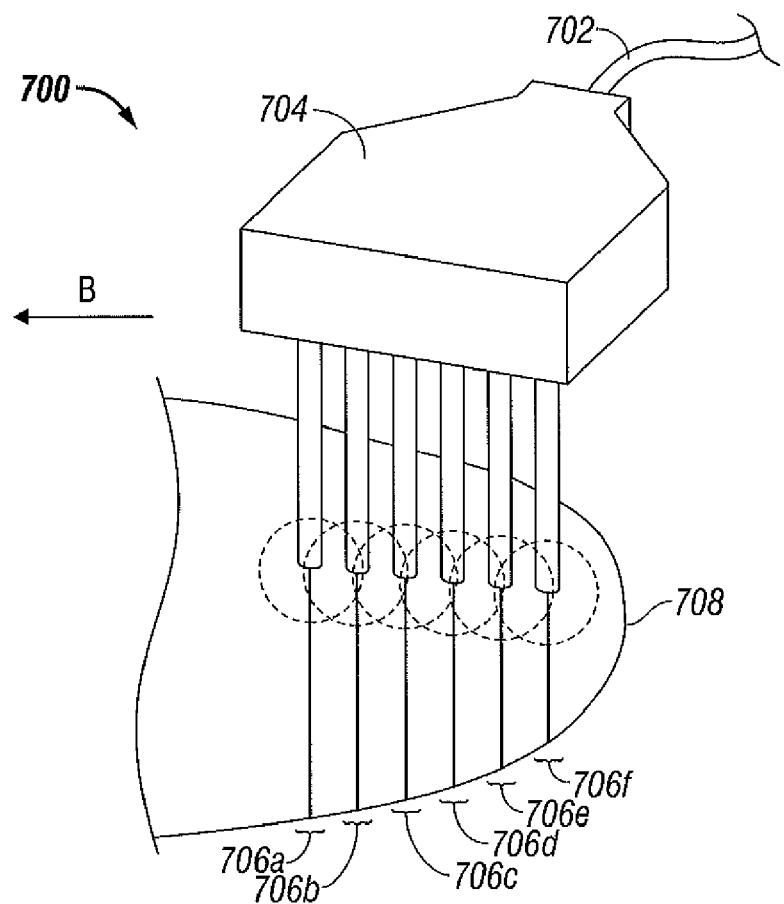
FIG. 7B shows a front-view of the surgical instrument of FIG. 8A in accordance with the present disclosure.

Referring to FIGS. 7A and 7B, surgical instrument 700 is shown for use with a resection procedure. FIG. 7A shows a side view of a surgical instrument 700 performing a resection procedure while FIG. 7B shows a front view of surgical instrument 700 ablating tissue to form an ablation plane for resection. Surgical instrument 700 includes cable 702, housing 704, and antennas 706a, 706b, 706c, 706d, 706e and 706f.

Ablation regions 710-718 are shown in FIGS. 7A and 7B, and correspond to different deployment states of antennas 706a through 706f. By varying the deployment state of one of the antennas 706a-706f, an aggregation ablation plane is formed that can resect a portion of organ 708. Referring to FIGS. 7A and 7B, each of antennas 706a through 706f has a different deployed state approximately central to organ 708, but deployable to different depths. The antennas 706a-706f form a longitudinal aggregate ablation region that overlaps with a longitudinal aggregate ablation region of an adjacent antenna forming an ablation plane for resection purposes.

Figure 8A:
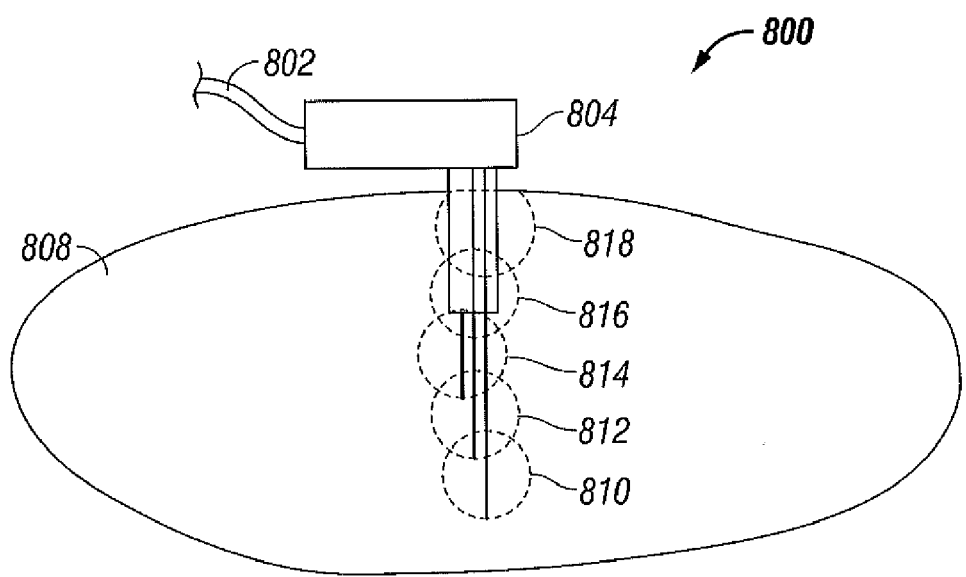
FIGS. 8A-8B shows two views of a surgical instrument having an assembly of antennas ablating tissue for resecting tissue along a curved plane in accordance with the present disclosure.
Figure 8B:
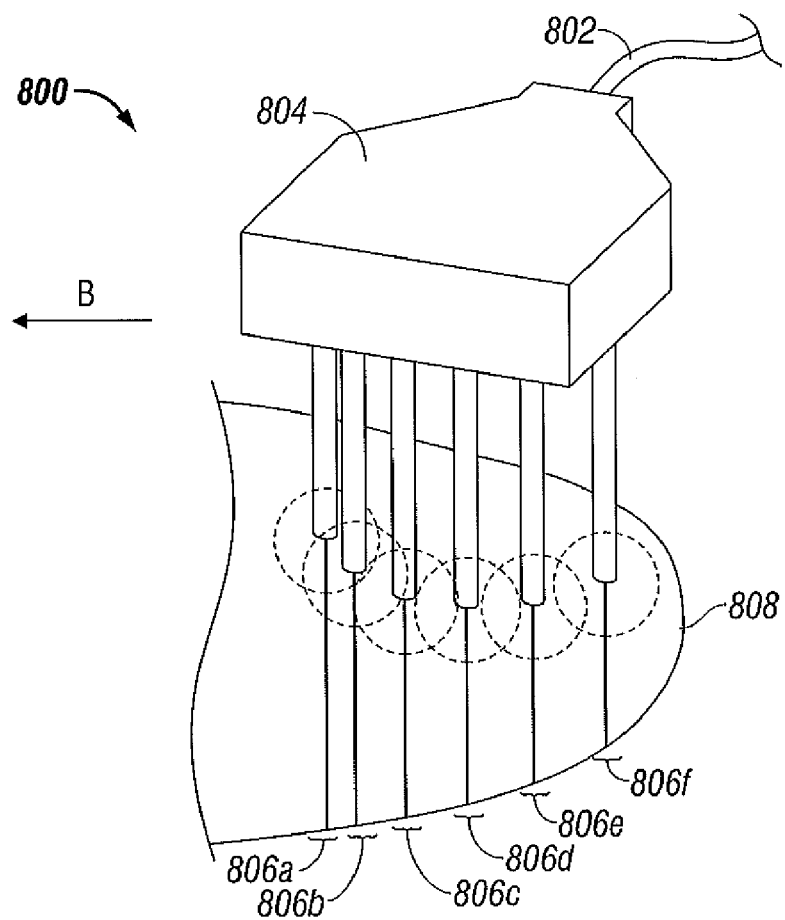

Referring to FIGS. 8A and 8B, surgical instrument 800 is shown and can be used during a resection procedure. Surgical instrument 800 includes a cable 802 connected to a housing 804. Surgical instrument 800 includes antennas 806a through 806f ablating tissue of organ 808. Surgical instrument 800 is similar to surgical instrument 700 of FIG. 7; however, antennas 806a through 806f of surgical instrument 800 form a curved ablation plane. More particularly, antennas 806a through 806f can be used to resect a curved region of organ 808.

Figure 9A:
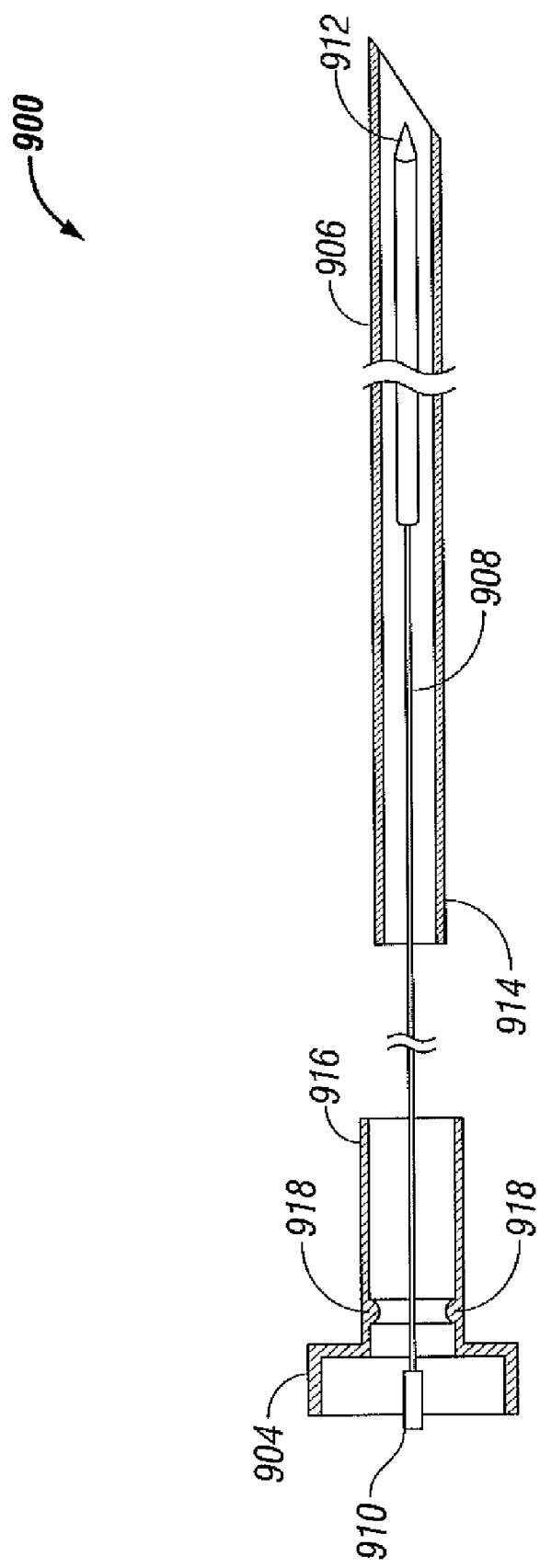
FIGS. 9A-9B are cross-sectional views of a deployable antenna in accordance with the present disclosure.
Figure 9B:
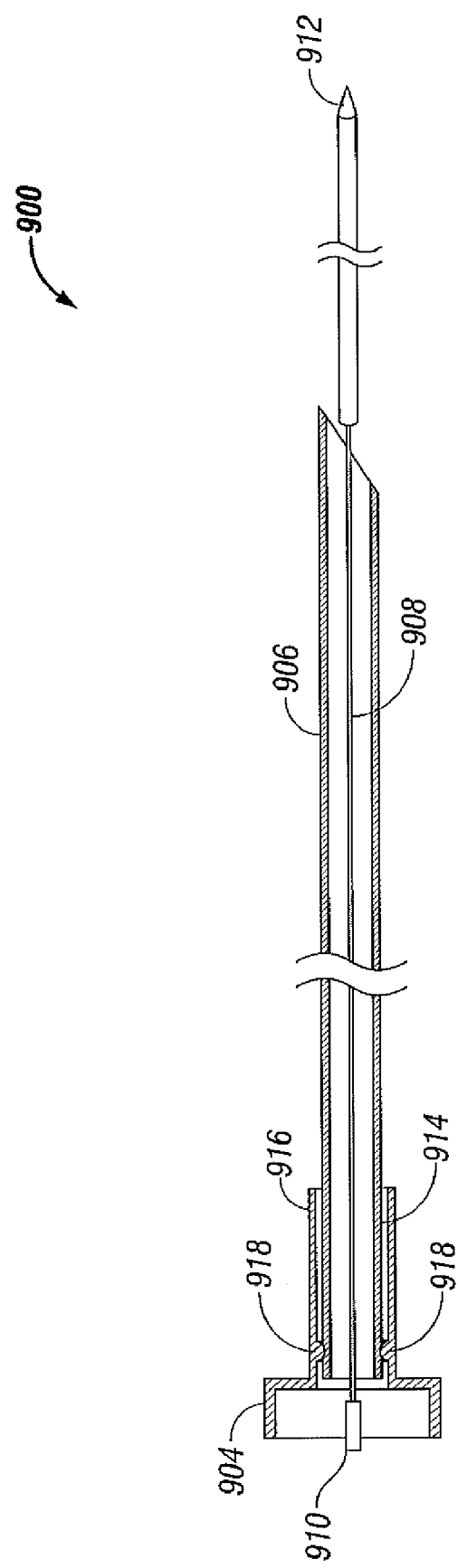

FIGS. 9A and 9B show a cross-sectional view of one variation for connecting a microwave generator (microwave generator 102 of FIG. 1) to an antenna 900 having a deployable state. In this variation, connector end 916 may extend from connector 904 and attach to a proximal end of feedline 906. Inner conductor 908 may extend throughout the length of the assembly 900 from pin 910, which may connect to a cable leading to a microwave power generator, and end in tapered end 912 for deployment within the tissue. FIG. 9A shows antenna 900 in a retracted state, while FIG. 9B shows antenna 900 in a fully deployed state. To advance tapered end 912 from closer proximity to feedline 906 toward tissue, receiving connector end 916 of connector end 916 may be advanced into contact with proximal end 914 of feedline 906. As connector end 916 comes into physical contact with proximal end 914, tapered end 912 is advanced away from feedline 306 in the direction of the tissue. Also, retaining member 918, which may simply be a protrusion or other fastener as known in the art, may provide a secure contact between connector shell 902 and feedline 906. Furthermore, retaining member 918 may be an electrically conductive contact such that it also provides a secure electrical communication path between connector shell 902 and feedline 906 to allow for the microwave energy to be transmitted between the two. This feature may also act as a safety feature in that tapered end 912 is preferably fully deployed before the electrical connection is made between feedline 906 and connector shell 902. However, in other embodiments, electrical contact is maintained in all deployment states or positions.

Figure 10:
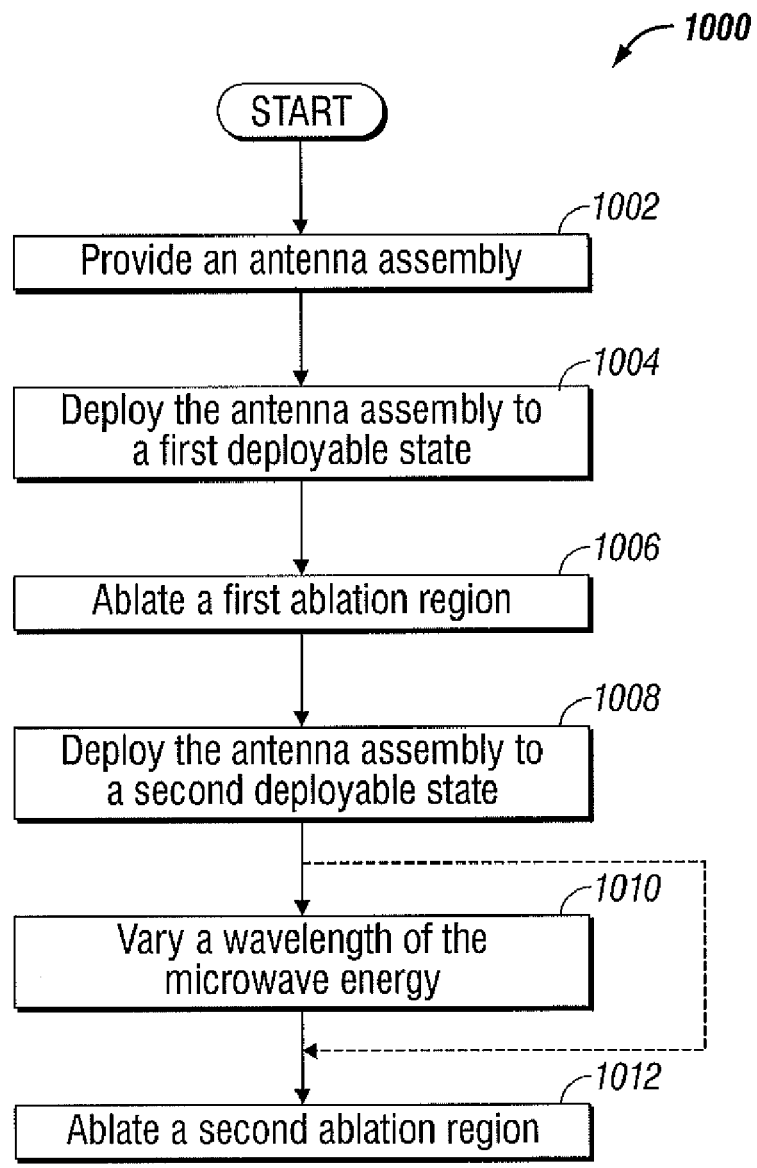
FIG. 10 is a flow chart of a method for treating tissue using a deployable antenna in accordance with the present disclosure.

FIG. 10 shows a method 1000 for treating tissue and includes steps 1002 through 1012. Step 1002 is providing an antenna, such as the antenna 300 of FIGS. 3A-3C. Step 1004 is deploying the antenna to a first state. Step 1006 is ablating a first ablation region. Step 1008 is deploying the antenna to a second deployable state. Step 1010 is varying a wavelength of the microwave energy. The wavelength of the microwave energy may be varied to account for the changing deployment state of the antenna. In some embodiments or procedures, step 1010 may be skipped. Step 1012 is ablating a second ablation region.

From the foregoing and with reference to the various figure drawings, those skilled in the art will appreciate that certain modification can also be made to the present disclosure without departing from the scope of the same. For example, the outer conductor may be movable relative to the inner conductor and a handle of the surgical instrument.

What is claimed is:

1. A microwave ablation system for treating tissue, the system comprising:
    an assembly of antennas adapted to connect to a microwave generator configured to generate microwave energy, each of the antennas in the assembly including:
    an inner conductor having a length; and
    an outer conductor having a longitudinal axis defined along a length thereof, the outer conductor at least partially surrounding the inner conductor at least partially along the length thereof, at least one of the inner conductor and the outer conductor movable with respect to the other;
    wherein at least one of the antennas in the assembly of antennas is deployable from a first state for ablating a first ablation region of tissue to a second deployable state for ablating a second ablation region of tissue, wherein the first and second ablation tissue regions overlap to define an aggregate ablation region.

2. The system according to claim 1, wherein the assembly of antennas are positioned to form, at least partially, a concentric ablation region.

3. The system according to claim 1, wherein at least two of the assembly of antennas are configured to form two overlapping aggregate ablation regions to at least partially form an ablation region.

4. The system according to claim 3, wherein the ablation region formed in tissue is curved along at least one radius.

5. The system according to claim 1, wherein the assembly of antennas includes first and second antennas, wherein the longitudinal axis of the first antenna is approximately parallel to the longitudinal axis of the second antenna.

6. The system according to claim 1, wherein the longitudinal axes of the assembly of antennas are approximately parallel.

7. The system according to claim 1, wherein the longitudinal axes of the assembly of antennas are approximately disposed in a planar region.

8. The system according to claim 1, further comprising:
    a connection hub including a plurality of cable connectors, wherein each of the plurality of cable connectors is coupled to each corresponding antenna of the assembly of antennas.

9. The system according to claim 1, further comprising:
    a connection hub including a cable connector and a semi-rigid coaxial cable, wherein the semi-rigid coaxial cable is coupled to an antenna of the assembly of antennas and to the cable connector.

10. The system according to claim 1, further comprising:
    a connection hub including a cable connector, wherein the cable connector is coupled to each of the assembly of antennas.

11. The system according to claim 10, the connection hub further comprising:
    a power splitter coupled to the cable connector and to at least one of the assembly of antennas, the power splitter configured to direct a predetermined quantity of the microwave energy to the at least one of the assembly of antennas.

12. The system according to claim 1, wherein at least one of the assembly of antennas further comprises: a dielectric material layer at least partially disposed between the inner conductor and the outer conductor.

13. The system according to claim 1, wherein at least one of the assembly of antennas further comprises: a tapered end having a tip disposed at one of the distal end of the inner conductor and the distal end of the outer conductor.

14. The system according to claim 1, the system further comprising a microwave generator which generates microwave energy at a plurality of wavelengths.

15. The system according to claim 14, wherein at least one of the assembly of antennas has an effective wavelength that is about equal to a corresponding wavelength of the plurality of wavelengths.

16. The system according to claim 14, wherein an antenna of the assembly of antennas has a variable effective wavelength and the microwave generator varies a first wavelength to be about equal to the variable effective wavelength of the antenna of the assembly of antennas.

* * * * *